United States Patent

Armstrong et al.

(10) Patent No.: US 8,284,809 B2
(45) Date of Patent: Oct. 9, 2012

(54) LASER BANDWIDTH INTERLOCK CAPABLE OF SINGLE PULSE DETECTION AND REJECTION

(75) Inventors: James P. Armstrong, Livermore, CA (US); Steven James Telford, Livermore, CA (US); Rodney Kay Lanning, Pleasanton, CA (US); Andrew James Bayramian, Manteca, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 390 days.

(21) Appl. No.: 12/729,138

(22) Filed: Mar. 22, 2010

(65) Prior Publication Data

US 2011/0170567 A1    Jul. 14, 2011

Related U.S. Application Data

(60) Provisional application No. 61/162,450, filed on Mar. 23, 2009.

(51) Int. Cl.
*H01S 3/00* (2006.01)
*H01S 3/13* (2006.01)
*G02B 27/10* (2006.01)

(52) U.S. Cl. ........... 372/38.09; 372/29.011; 372/29.014; 359/618

(58) Field of Classification Search ............... 372/25, 372/29, 29.011, 29.014, 29.02, 30, 38.1, 372/38.09; 356/300–334; 359/618
See application file for complete search history.

(56) References Cited

U.S. PATENT DOCUMENTS

| 4,758,086 | A  | * | 7/1988  | Sonobe et al. ................. 356/327 |
| 4,785,292 | A  | * | 11/1988 | Kern et al. ..................... 340/578 |
| 5,764,666 | A  | * | 6/1998  | Wakabayashi et al. ..... 372/38.09 |
| 2009/0213371 | A1 | * | 8/2009 | Goodyer et al. .............. 356/319 |
| 2011/0058166 | A1 | * | 3/2011 | Nakamura et al. ............ 356/327 |

* cited by examiner

*Primary Examiner* — Jessica Stultz
*Assistant Examiner* — Phillip Nguyen
(74) *Attorney, Agent, or Firm* — John P. Wooldridge

(57) ABSTRACT

A pulse of laser light is switched out of a pulse train and spatially dispersed into its constituent wavelengths. The pulse is collimated to a suitable size and then diffracted by high groove density multilayer dielectric gratings. This imparts a different angle to each individual wavelength so that, when brought to the far field with a lens, the colors have spread out in a linear arrangement. The distance between wavelengths (resolution) can be tailored for the specific laser and application by altering the number of times the beam strikes the diffraction gratings, the groove density of the gratings and the focal length of the lens. End portions of the linear arrangement are each directed to a respective detector, which converts the signal to a 1 if the level meets a set-point, and a 0 if the level does not. If both detectors produces a 1, then the pulse train is allowed to propagate into an optical system.

19 Claims, 11 Drawing Sheets

LASER BANDWIDTH INTERLOCK CAPABLE OF SINGLE PULSE DETECTION AND REJECTION

CROSS-REFERENCE TO RELATED APPLICATIONS

This application claims priority to U.S. Provisional No. 61/162,450, titled "Laser Bandwidth Interlock Capable of Single Pulse Detection and Rejection" filed Mar. 23, 2009, incorporated herein by reference.

STATEMENT REGARDING FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC.

BACKGROUND OF THE INVENTION

1. Field of the Invention

The present invention relates to techniques for preventing laser damage to optical systems, and more specifically, it relates to a pulse bandwidth analysis interlock.

2. Description of Related Art

Modern laser systems often require broad bandwidth for short pulse applications, driving high energy density physics experiments, or suppression of nonlinear effects in optical materials. Laser architectures designed to deliver this broad bandwidth can often be damaged if the laser bandwidth is too low. The use of bandwidth is generally done to suppress nonlinear optical effects that are bandwidth dependent, to enable smoothing by spectral dispersion or to enable a pulse to be stretched in time for amplification. Often a system is built to rely on this bandwidth since the fluence may be safely increased in fiber or bulk systems with the presence of bandwidth or a stretched pulse. However, once the system is designed this way, catastrophic damage to high value systems can occur if even a single pulse is generated without bandwidth. A spectral interlock is desired that is able to evaluate an individual pulse from a pulse train to ensure it meets minimum bandwidth requirements and, if not, remove that pulse from the pulse train. It is further desirable that the system is flexible enough to allow use over a broad range of bandwidths encountered in the marketplace. It must run at a broad range of repetition rates, from shot-on-demand to e.g., 5 MHz.

BRIEF DESCRIPTION OF THE DRAWINGS

The accompanying drawings, which are incorporated into and form a part of the disclosure, illustrate embodiments of the invention and, together with the description, serve to explain the principles of the invention.

SUMMARY OF THE INVENTION

Figure 1A:
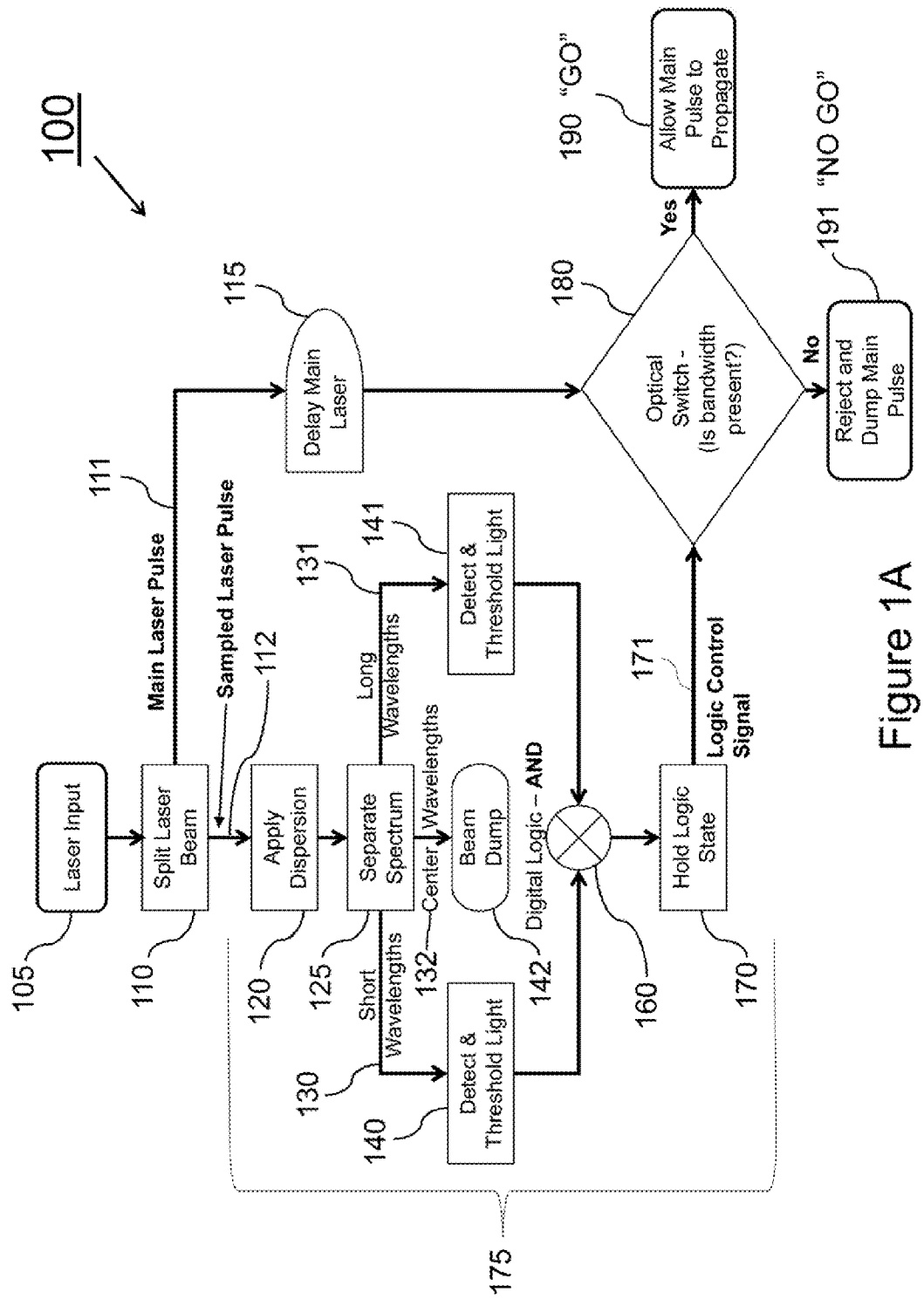
FIG. 1A shows a system flow chart of an exemplary embodiment of the present invention.

The various embodiments described below are generally referred to as Spectral Sentry. An embodiment of the present invention includes a compact automated interlock which detects bandwidth, delivers a positive signal if bandwidth minimum requirements are met, and can stop low bandwidth pulses from propagating further. A pulse is brought in to the device where the spectrum is dispersed across an image plane. Once sufficient separation has been achieved, a portion of the red and blue side of the spectrum representing the minimum bandwidth, are reflected to two independent detectors for conversion to electrical signals. To eliminate false positives, each signal must meet a minimum intensity requirement, whereupon the two signals are logically combined such that both the red and blue must be present to yield a positive result, which indicates the presence of sufficient bandwidth. Each pulse that is determined to contain insufficient bandwidth is removed from the pulse train either within the device itself (utilizing optical switching) or by interrupting the timing signals to subsequent optical systems downstream of the device.

This system may be used for protecting pulsed laser systems. It is ideally suited for fiber-based Master Oscillator Power Amplifier (MOPA) lasers that generate bandwidth external to the oscillator, but can also be used in non-fiber or mode-locked systems. Embodiments of the present invention were invented for use on the Mercury laser at Lawrence Livermore National Laboratory (LLNL). In this system, single shot, speed-of-light spectral interlocks are viewed as a required technology for future high-repetition rate systems where a single shot without bandwidth can cause optical damage. Such a technology is a critical component for a solid state inertial fusion energy system that utilizes phase modulation for suppression of non-linear effects and beam smoothing by spectral dispersion. Potential future market could be significantly expanded if solid-state drivers are utilized for inertial fusion energy.

Commercial uses of the present invention would focus on a device that would protect lasers systems that may be damaged by a pulse that does not contain the expected bandwidth. The systems on which the device may be deployed are not limited to only phase modulated systems, although it is well suited for that application. The device may be used, e.g., on any pulsed laser system that requires a minimum bandwidth and has some method of delaying the main signal pulse (fiber, polarization confinement, propagation distance, etc) sufficiently to allow for analysis and rejection of the pulse.

The laser pulse train to be analyzed can be introduced to the system, e.g., through an optical fiber or by free-space alignment. A portion of the beam is split off for analysis while the remainder is allowed to propagate. The analysis beam is collimated to a suitable size (typically 1 mm diameter) and directed to an optical system to disperse the spectral components of the light spatially. This can be done with two multilayer dielectric coated diffraction gratings where the beam and gratings are aligned in such a way as to make four bounces off the gratings (two bounces per grating) to increase the amount of dispersion and, therefore, angular separation between the spectral components of the laser. This large dispersion is needed because phase modulated bandwidth can be quite small, typically less than 1 nm. The output of the dispersive system is then brought to the far field by passing it through a focusing system with its parameters chosen to produce the desired separation of colors at the focal plane. Two mirrors are then aligned to reflect the red and blue portions of the spectrum to a pair of high-speed photodiodes. The mirrors can be two prisms with reflective coatings applied to their hypotenuse. The prisms are separated to allow the center portion of the spectrum to pass between them without being reflected to the detectors. The separation of the prisms can be altered to dictate the minimum bandwidth required. to activate the interlock.

When each side of the laser spectrum falls upon its respective detector, the optical signals are converted to electrical signals. The analog electrical signals from both detectors are then converted to separate digital logic levels by utilizing an adjustable threshold comparator. Logic high levels are generated whenever light sufficient to exceed the electrical threshold is present on the detector. Additionally, the logic high levels can be made to persist after the end of the laser pulse, e.g., for more than 50 ns, to ensure that the logic signals from both detectors are present in subsequent electronics regardless of small optical or electrical signal propagation time differences. The signals from the two comparators are then logically combined to produce a single signal indicating that both detectors saw light at the same time. The reason for two detectors is to ensure that the interlock does not give a false "Go" signal from a simple misalignment of the optical system or from a spurious electrical signal. The logical AND output is then fed in to a gated latch where the logic signal indicating the presence or absence of bandwidth is held until the device receives an external trigger indicating an additional pulse is to be analyzed. This latched signal is sent to several outputs and drivers to enable triggering of other devices which may require high impedance or low impedance drive signals. Providing the user with the ability to manipulate secondary inputs to the latch enables two modes of operation in which the interlock signals a logic low (absence of bandwidth) only for the duration of the timing cycle (self reset mode) or in which the output remains low indefinitely until the user resets the system (latch mode).

The main signal pulse that had a portion split off for analysis must be stopped if insufficient bandwidth is detected. To accomplish this, the main signal must be delayed long enough to do the analysis and allow time for electrical signal to propagate to the device that will reject the pulse. A simple method for doing this is a fiber delay loop internal to the device itself in a fiber based system. For free space versions the user can provide some polarization confinement method or long propagation path to provide the required delay.

This forms a basic version of the device that can be used to interrupt timing signals to the user's external components. An acousto-optic switch may also be placed at the end of the delay fiber (for fiber-based versions) to provide a fully self-contained device that will not allow any light out of it which does not contain at least the minimum required bandwidth.

Spectral Sentry is an advanced technology designed to protect critical laser systems from errant pulses that contain insufficient bandwidth for amplification or experimental purposes. The device inspects each individual laser pulse generated by the laser it is protecting and determines if each pulse meets the minimum bandwidth requirements to avoid self-destruction. This assessment is done so rapidly that the Sentry device can stop the speed-of-light pulse it just measured from further amplification where it could potentially damage the machine.

DETAILED DESCRIPTION OF THE INVENTION

An exemplary embodiment of the laser bandwidth control system 100 according to the present invention is shown in FIG. 1A. An optical beam is provided from laser input 105. The beam is typically a very short-duration pulse, which may be a single pulse or one pulse in a sequence of short pulses. A typical pulse width can be in the range of approximately $10^{-8}$ seconds to less than $10^{-15}$ seconds, depending on the specific application, such as inertial laser fusion, material processing, laser communication, spread spectrum encrypted data, directed energy weapons, medical applications, etc. In these and other applications, it is critical that each laser pulse propagates within the system, as well as emerges from the apparatus, without substantial temporal degradation, which, in this case, is defined as a final pulse with less bandwidth than expected, or, equivalently, a pulse whose temporal duration is longer than expected, or, a pulse whose shape acquires undesirable temporal features. For example, a laser ablation system, designed for a materials processing system, laser drilling, a directed weapon system, etc., or a laser ablation system intended for medical applications, can result in an undesirable thermal excitation/melting mode as the pulse width increases. Another example pertains to optical communication, spread-spectrum links, etc: an unanticipated change from a high bandwidth to a low bandwidth source can render various communication systems corrupt at best, and, in some cases, nonfunctional.

The goal of the interlock system of the present invention is to determine if the bandwidth of a given laser pulse is consistent with that expected, at one or more predetermined locations within a laser system, and, further, to eliminate the given pulse from the system at one or more predetermined locations if the bandwidth requirement is not satisfied. More specifically, it is crucial that the bandwidth of each and every pulse be evaluated, since, even a single pulse with a reduced bandwidth can be deleterious to the given application or even result in irreversible optical damage within the laser system or to the workpiece. Hence, the system must be capable of evaluating each and every pulse. The key result of the interlock system involves a "go"/"no-go" decision process for each and every pulse. The interlock device will allow a given pulse to continue to propagate within the system if the bandwidth criterion is satisfied; and, block the beam otherwise, thereby preventing any and all degraded pulses from continuing to propagate within the apparatus. Note that this interlocking device can be placed at any location within a given laser system, as well as at multiple locations, as necessary, with hard-wired or wireless control signals. Moreover, the location of the pulse sampling/evaluation apparatus can, in general, be at a different location in a given system relative to that of the optical interlock device.

As discussed below in more detail, the present invention can be configured in at least two modalities. One modality is referred to as an "auto-reset mode" and the second modality as a "latch mode." In the former case, each laser pulse in a given input sequence is analyzed for its bandwidth, with the system interlock functional state being completely independent relative to all other pulses in a given pulse sequence. Hence, given the presence of a pulse of insufficient bandwidth (which would require interlock activation), all subsequent pulses will be independently analyzed anew. That is, the system resets itself to analyze a subsequent pulse, independent of the interlock state for the previous pulse. In the "latch mode," once the interlock is activated to prevent transmission of a given pulse possessing insufficient bandwidth, all subsequent pulses are also suppressed, regardless of their respective bandwidths. That is, the interlock does not allow further pulses in the sequence to propagate in the system. The "latch" modality, therefore, requires some form of intervention before enabling the system to resume pulse-bandwidth interrogation --- be it operator intervention, computer intervention or a combination thereof.

Returning to FIG. 1A, the input laser from laser input 105 is incident upon a beam splitter 110. In the case of a free-space laser system, 110 can be a bulk optical flat with a given partially reflective coating. In an optical fiber system, 110 can be a 1x2 fiber coupler, so that all beam paths remain in guided-wave elements and devices. The beam splitter 110 directs most of the beam energy along optical path 111 to an optical delay line 115 while sampling a minimal amount of energy along path 112 for evaluation by the interlocking diagnostic system. Given the sensitivity of typical optical detectors, which can detect µJoules of energy or less, the fractional energy required to perform the bandwidth evaluation may be a very small fraction of the energy in the input beam. As an example, assuming a beam energy of ≈1KJoule, the sampled beam will only require $10^{-6}$ of the incident energy. An optional optical fiber 20 dB amplifier (not shown) along path 112 can further reduce this fraction by a factor of 100, so that, in this example, element 110 need only sample $10^{-8}$ of the input beam energy for interlock evaluation. (In the case of additional amplification, the optical amplifier must function over a bandwidth in excess of that expected for a typical incident beam, which is within the art). In short-pulse fiber systems, the energy per pulse can be in the mJoule range. Hence, the fractional sampled beam will require $10^{-3}$ or less of the incident energy. In either case, the sampled pulse will not materially affect the overall system performance, both in terms of energy efficiency as well as temporal bandwidth fidelity.

The main laser pulse 111 is incident upon an optical delay network 115 whose delay time is chosen to be greater than the total time required for the bandwidth evaluation and the interlock control to function, which can be in the range of 20 nsec or more. The required time for the interlock system to function stems from optical transit times within the sampling system and electrical device delays. A similar or greater time delay must, therefore, be applied to the main laser pulse leg of the system so that the interlock can eliminate a given pulse if the bandwidth condition is not satisfied. The necessary time delay to apply to the main pulse beam can be derived from two sources: Inherent propagation delays in the overall system configuration and, additional time-delays, as needed, applied via delay modules placed in the path of main laser pulse. Inherent time delays can be the result of physical location of the interrogation system relative to that of the interlock hardware placed along the beam path. Since many laser systems involve long propagation paths between critical components, say fiber delivery systems, amplifier chains, nonlinear optical elements, lenses, beam combiners, etc the physical positioning of the interlock hardware may result in propagation delays. Note also, that since the control signal can be sent over a point-to-point link, whereas a laser system may involve complex, folded beam paths, this can also contribute to the inherent time delay.

A second source of a time delay, if needed, can be realized via the insertion of a time-delay module in the path of the main laser beam. Candidate free-space and fiber-based approaches to realize the required time delay exist in the art, with the requirement that the delay network maintain the bandwidth of the main laser pulse. Examples of free-space delay modules include multi-bounce optical cavities such as so-called "White Cells" and polarization-based delay lines. Fiber and optical waveguide delay lines, be they single-pass or multiple-pass, can service free-space as well as guided-wave systems. The guide (e.g., optical fiber) must be chosen to preserve the bandwidth as well as possess minimal linear and nonlinear dispersion, which would otherwise degrade the temporal shape of the main laser pulse. Given that the required delays are in the range of 10s of nsec, the length of fiber can be relatively short, in the range of several meters to 10s of meters. This short length of fiber is not expected to materially affect the main laser pulse bandwidth or pulse shape. For longer time. delays and/or in the case of extremely high peak-powers, one can utilize a Noble gas (Xe) filled hollow-core photonic crystal fiber for high bandwidth, guided-wave optical transmission, without such deleterious nonlinear effects as Brillouin and Raman scattering, as well as nonlinear phase shifts. Xe, being in its atomic form, does not possess rotation/vibration manifolds, hence Raman scattering does not exist. Moreover, nonlinear phase shifts are minimal in a noble gas medium. Furthermore, the Xe fill pressure can be chosen to minimize Brillouin scattering. In addition, a photonic crystal fiber can he engineered to possess minimal material and/or waveguide dispersion.

Returning to FIG. 1A, attention is directed to the sampled laser pulse portion of the embodiment. The sampled laser pulse 112 is incident upon a spectral analysis subsystem, comprised of dispersive network 120, which, in combination with an optical configuration 125, provides three spatially dispersed output beams, all derived from the spectrum of the input pulse: one beam consists of the short wavelength region 130 of the pulse spectrum; a second beam consists of the long wavelength region 131; and, the third beam consists of the central wavelength region 132 of the pulse spectrum. This subsystem is basically an optical spectrometer with a given dispersion and bandpass network. As discussed below in reference to FIG. 2, the wavelength range and wavelength centroid of each spectral band can be preset by the end user for a given application. In the embodiment shown in FIG. 1A, two wavelength bands (the low and high regions) of the pulse spectrum are each detected using a fast photodiode and compared against respective reference threshold levels, 140 and 141. In this embodiment, the optical power in the central region of the spectrum is discarded. However, situations exist whereby all the three wavelength regions require evaluation. As an example, there are cases whereby several, or even all, spectral modes in a mode-locked laser may intermittently lose phase locking. In this situation, the central wavelength power level may increase relative to the low and high spectral regions, resulting in lengthened output pulses or even intermittent, continuous-wave operation (i.e., no pulses, only a steady output power). This situation can result in potential optical damage within the system as well as irreversible damage to the end-user workpiece.

Returning to FIG. 1A, the optical level of each given spectral band provides input to a respective comparator, where it is compared against a predetermined respective reference value to determine if each given power level satisfies a respective threshold condition. The output of each comparator can be in the form of a digital logic level (e.g., a TTL voltage). The pair of digital signals are input into a logic network comprised of a digital logic AND module 160, a hold-logic state device 170 and a logic-controlled optical switch 180. The logic network takes this information and either opens the optical interlock 180 to allow the main pulse to continue in the overall system, via path 190 --- in the case of sufficient pulse bandwidth; or, closes the optical interlock 180 to prevent the main pulse from continuing to propagate in the overall system, via path 191 --- in the case of insufficient pulse bandwidth. Typically, the interlock is set to a normal "off-state" (i.e., no light is allowed to pass) to minimize the chance of a low bandwidth pulse from passing through this critical checkpoint, which can otherwise be extremely deleterious to the overall system and its end-use application. The interlock apparatus can be a free-space or guided-wave electro-optic or acousto-optic activated network, depending on the specific system configuration, peak-power levels, operating wavelength, etc.

It is important to configure the system to minimize false alarms (both positive and negative) from either allowing low-bandwidth pulses to pass without rejection as well as mislabeling a high-bandwidth pulse as one to be rejected. The former misidentification can result in system damage as discussed elsewhere. The latter case can result in terminating all pulses subsequent to the misidentified (high-bandwidth) pulse if the system is operated in the latch mode. To minimize the latter scenario, the system is configured to indicate sufficient (high) bandwidth if both the high-wavelength as well as the low-wavelength logic levels are in the "1" state. Hence, if only one of the two spectral indicators are sensed to be above its threshold state, this can be the result of a system misalignment (or other optical/electrical malfunction), and, not necessarily due to the presence of a sub-bandwidth pulse. Therefore, in this case, it may not be accurate to enable the "latch mode" function to reject all subsequent pulses, but, instead to indicate a potential system failure (instead of a laser malfunction).

Figure 1B:
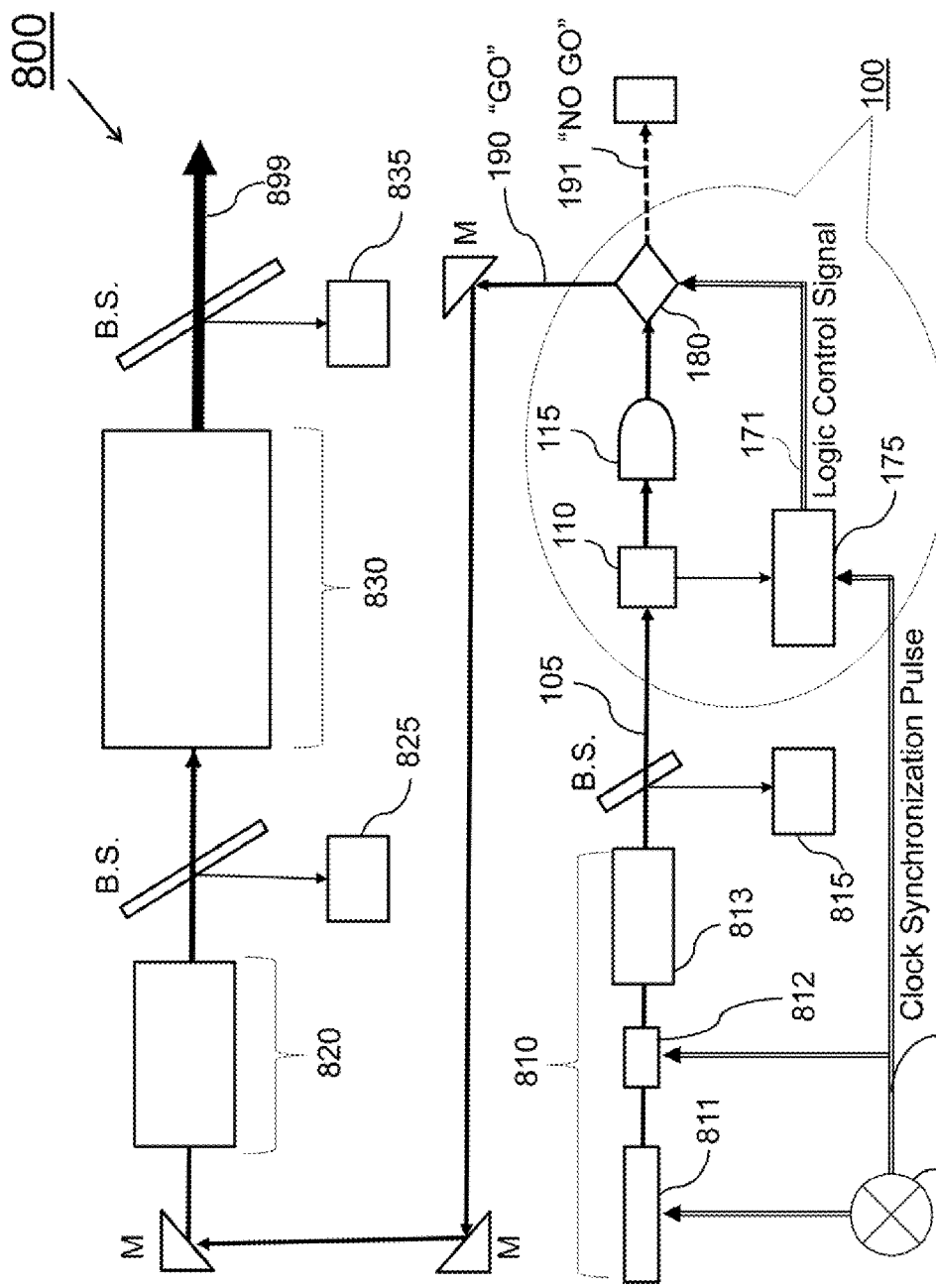
FIG. 1B shows a drawing of a three-stage master oscillator, power amplifier laser system that incorporates the bandwidth interlock shown in FIG. 1A.

Turning now to FIG. 1B, an example is shown of an overall laser system, 800, comprised of a three-stage master-oscillator, power-amplifier (MOPA) laser system that incorporates the bandwidth interlock system 100 embodiment discussed in reference to FIG. 1A. A system similar to that shown in FIG. 1B has been successfully demonstrated and shown to differentiate amongst laser pulses that meet (or exceed) a preset minimum spectral bandwidth from those pulses that do not; and, to subsequently control an optical interlock that passes or rejects each and every pulse in a given pulse sequence, the results of which will be discussed in detail below.

The representative laser system shown in FIG. 1B consists of three stages that result a high-energy output beam 899. The first stage is a low-energy, master oscillator subsystem, 810, comprised of a pulsed seed laser, 811, a gateable 60 GHz phase modulator, 812, and an optical preamplifier, 813. The second, or, intermediate stage, 820, is comprised of a medium-power laser amplifier, which can be configured in a serial and/or parallel arrangement of amplifiers, as is known in the art. The final stage, 830, is comprised of a high-power optical amplifier, which, again, can be configured in a serial and/or parallel manner.

A master-clock module 172 establishes synchronization-timing pulses 173 that control the overall laser system, including the interlock controller. Various diagnostic devices can be located throughout the system to monitor its performance, etc. In this example, optical energy measurements are recorded at the output of each respective stage of the three-stage MOPA system. A very small fraction of the laser beam energy is derived from three respective beam splitters (labeled as "B.S." in the figure), and directed to respective energy meters, 815, 825 and 835, as shown in the figure. Typical arrangements of folding mirrors (labeled as "M" in the figure) direct the laser beam from one stage to the next, and, so on. In the experimental demonstration to be discussed below, the 60 GHz phase modulator, 812, is used to add bandwidth to the seed laser pulse, which is required to circumvent narrow-spectral band induced optical damage and/or deleterious nonlinear optical effects, including, but not limited to, stimulated Brillouin scattering.

In the laser system shown in FIG. 1B, the spectral interlock system is placed between the first and second stages of the overall system in this example. The results of the spectral analysis subsystem 175 control the optical. interlock 180 via control signal 171. If the spectral conditions are satisfied, the interlock is switched into the "go" position, and the main beam 190 is then directed to the subsequent second-stage amplifier 820 and subsequent stages, resulting in a final high-energy output beam 899. If, on the other hand, the first-stage spectral conditions are not satisfied, as analyzed by the module 175 of the interlock system 100, the interlock 180 will reject the given pulse (the "no go" condition) and switch the beam 191 toward a beam dump. The optimum choice for the placement of the sampling beam pickoff module 110, the main-beam time-delay module 115, the spectral sampling/analysis/logic control subsystem, 175, and the "go"/"no-go" optical switch 180, will be a function of the specific end-user laser system, the energy expected at various positions along the beam line and the critical locations in the system where optical damage may occur in the event of a system malfunction.

Figure 2:
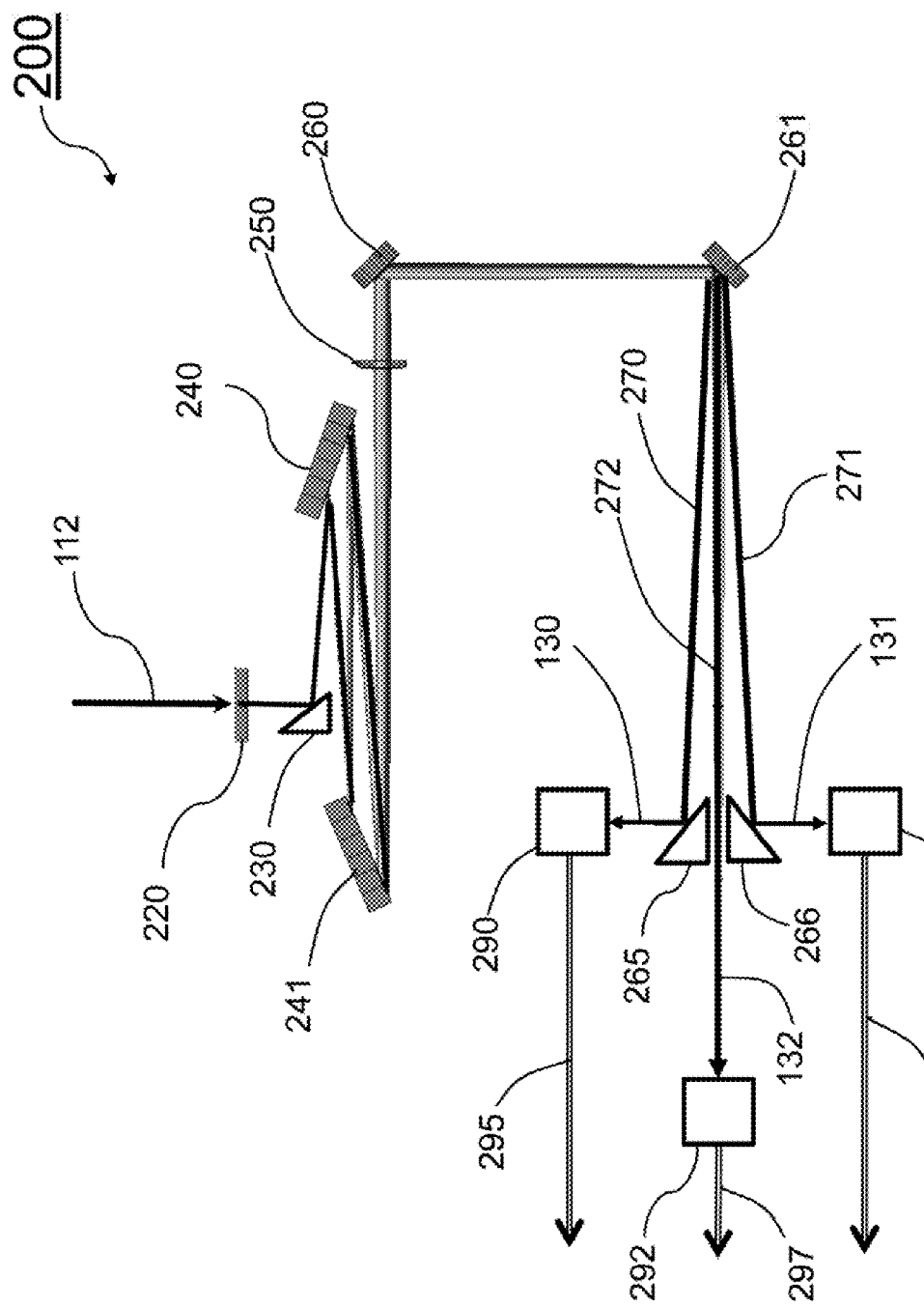
FIG. 2 shows a drawing of an exemplary embodiment of the laser wavelength spectral analyzer subsystem, which includes an optical dispersive network, comprised of a pair of gratings and, further, includes a three-port optical bandwidth detection network, comprised of three detectors, with each detector sampling a different wavelength region of the input beam spectrum.

Turning now to FIG. 2, a drawing is shown of a spectral analysis subsystem 200 in more detail, which is comprised of two key functional components: an optical dispersive network and a set of high-speed optical detectors. The spectral analysis subsystem is basically an optical spectrometer with a given dispersion and a multi-wavelength bandpass network, with independently adjustable spectral bandpass filters. The sampled beam 112 is incident upon a beam collimator 220 resulting in a beam in the range of 1 mm in diameter, and is then incident upon a folding prism mirror 230, directing the pulsed light to an optical dispersing system. In this embodiment, a multi-optical grating dispersive system is shown, which, in this case, consists of a pair of multi-layer dielectric coated grating elements 240 and 241. The dispersion can be determined by the end-user for a given pulse bandwidth application, and can be designed by the choice of the dispersive optical configuration (one-pass, multi-pass gratings, etc.) and/or by the grating dispersion (e.g., in terms of the grating lines per mm, etc.).

The spectrally dispersed output from the grating pair is subsequently transformed into the far-field by a combination of optical element 250, along with a pair of folding mirrors 260 and 261, resulting in a spatial mapping of the pulse spectrum. In a typical embodiment, the optical system is configured for four bounces off of 1780 line/mm gratings and a mirror spread of 760 μm at the far field. In this embodiment, the dispersive capability was in the range of 0.29 nm/mm. This large dispersion (i.e., high spectral resolution) is needed because typical phase-modulated bandwidths can be quite small, typically less than 1 nm. With amplified detectors, the system easily provides reliable detection of bandwidths of 60 GHz (0.25 nm) or greater.

In selected high-energy laser applications, this bandwidth is intentionally imposed onto laser pulses to spread out its spectrum, thereby circumventing optical damage of critical components in the laser system. If the 60 GHz modulator malfunctions, even for one pulse, catastrophic optical damage may result in the high-energy stages of a typical laser system. Hence, this so-called point-failure must be evaluated for each laser pulse to eliminate each and every deleterious low-bandwidth pulse from the system.

The spatially and spectrally dispersed beam is effectively partitioned into three spectral regions, a short wavelength band 270, a long wavelength band 271 and a central band 272. This set of three spectral bands is incident upon a compound optical component capable of fine-tuning the bandpass of the sampled spectrum and its spectral centroid. In this embodiment, the compound optical component is comprised of a pair of opposing folding prisms 265 and 266. The prisms are configured so that a parallel gap separates the prism pair. The beams that reflect from the prism mirrors, 130 and 131, are directed to respective high-speed detectors, 290 and 291. The beam that emerges through the prism gap 132 is directed to high-speed detector 292. (For applications that only require the relative optical energy in the spectral extremities, element 292 is in the form of a beam dump, as shown in FIG. 1A.) In general, each of the three spectral bandpass filter functions is adjustable, which is determined by the transverse positions of the prism pair and gap that separates them. The respective output signals from the three detectors, 295, 296 and 297 are then directed into a control logic module, discussed next.

Figure 3:
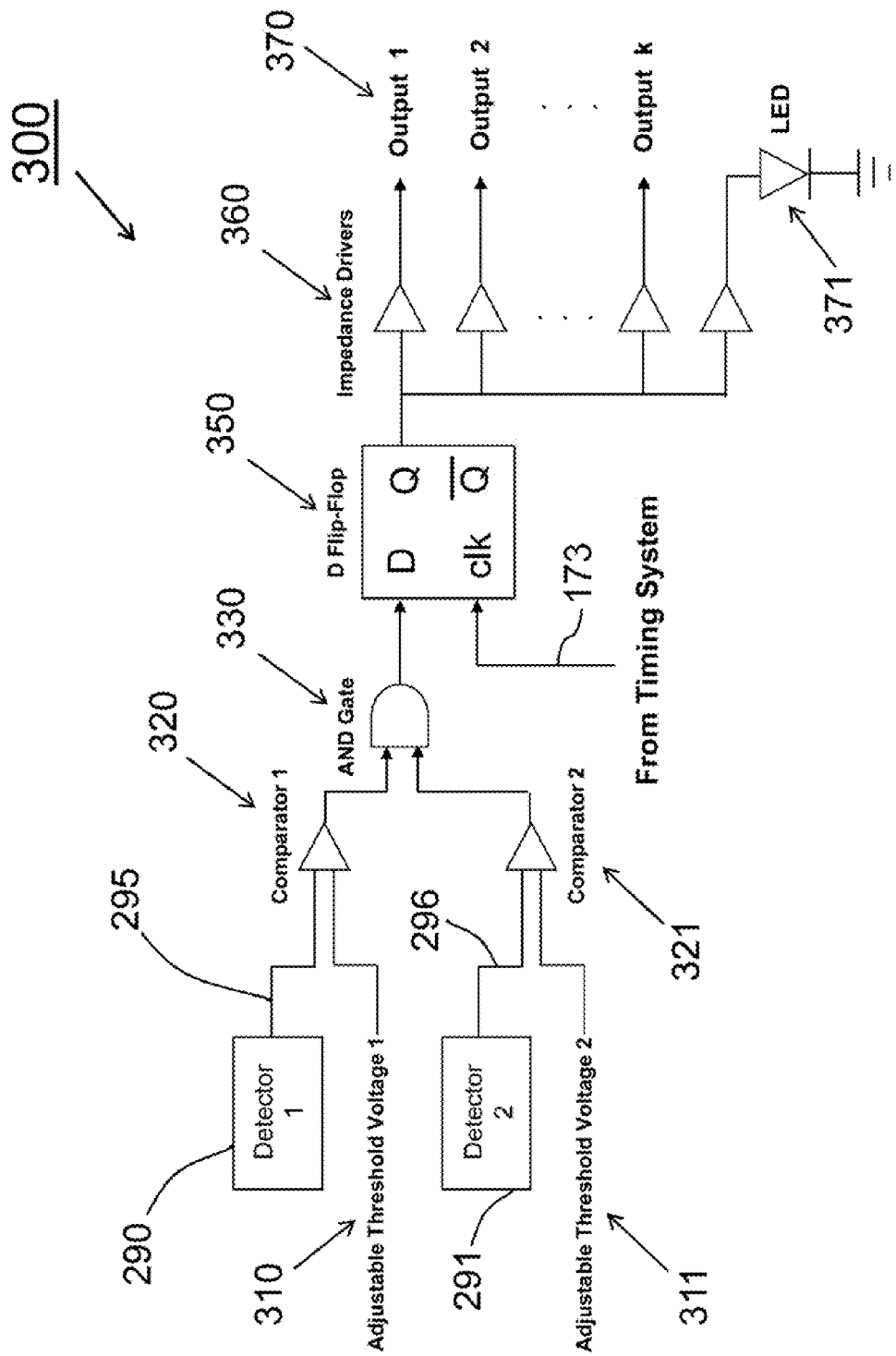
FIG. 3 shows a drawing of an exemplary embodiment of the electronic logic subsystem circuit, to address a two-port spectral sampling system, comprised of a pair of comparators, a logic AND gate and a D-flip-flop module, whose multiple outputs control overall system triggers, interlocks and other diagnostics.

FIG. 3 shows a schematic circuit drawing of a control logic module 300, in the case of a pair of spectral bands to be analyzed (here, the central wavelengths are directed to a beam dump, as discussed above). The basic functions of this module are depicted in FIG. 1A as respective detector and threshold elements 140 and 141; and as respective logic-AND combiner and hold-state logic elements 160 and 170. Returning to the details of this embodiment as shown in FIG. 3, the inputs to this module consist of the respective detector output levels, 295 and 296; respective threshold levels, 310 and 311; and a clock trigger synchronization pulse, 173, as generated by a master trigger module 172. As discussed above, to establish that the pulse spectrum has sufficient bandwidth (based on system design rules), and, further, to minimize false alarm rates, the spectral energy in both extreme spectral bands --- the short-wavelength and long-wavelength regions --- must exceed a predetermined minimum threshold level, and, further, must both be present simultaneously as well as temporally coincident with the main laser trigger synchronization timing pulse. The threshold levels are provided independently, via respective threshold voltages 310 and 311, to each respective comparator 320 and 321. A logic-AND gate 330 provides a TTL on-state level when these two threshold conditions are satisfied. The AND-gate TTL output provides one input to the D-flip-flop module 350. The other input to 350 is a synchronization pulse 173 from the timing system 172, which, when present simultaneously with the AND-gate output, will provide a set of parallel (TTL) outputs 370 via respective impedance drivers 360, and, an optional LED output 371 for operator monitoring. The signals can be maintained in a latch mode long enough for the laser's timing cycle to complete. These signals may also be used as a per-pulse go/no-go input to the laser's external timing system, or can be used to trigger an integrated optical gate when used in an inline configuration. Note that the presence of a temporally coincident timing system pulse, with that of a bandwidth acceptance TTL level, minimizes false alarms.

Figure 4:
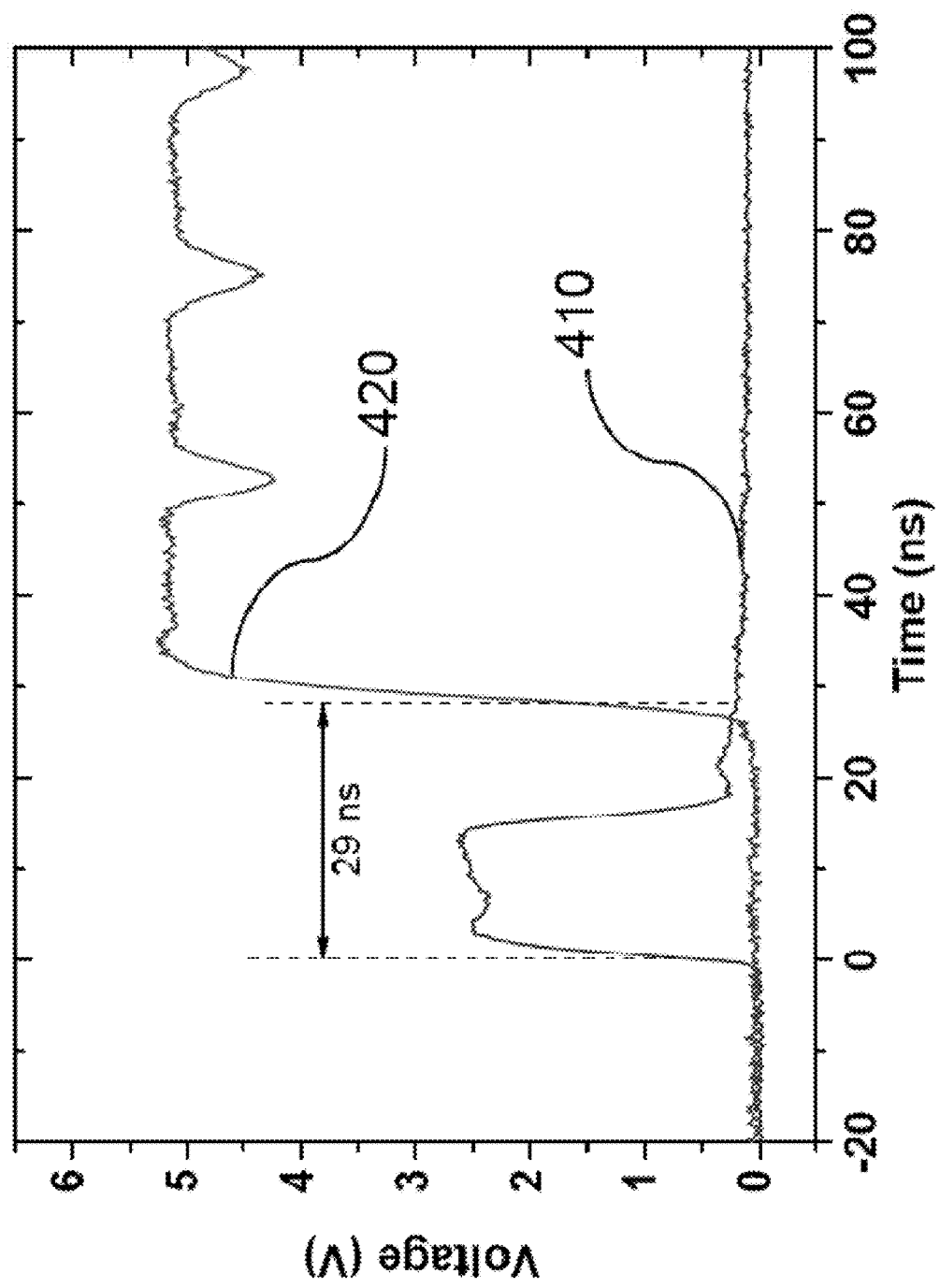
FIG. 4 shows results of a measurement to characterize the response time of the system shown in FIG. 1A.

FIG. 4 shows results of interlock system response-time measurements, as defined from the onset of an optical signal detector pulse to the generation of an interlock signal that controls the main laser beam. The response time is equal to the total optical and electrical transit times acquired by the sampling laser pulse as it is spectrally dispersed, its spectrum detected, analyzed for sufficient bandwidth and spectral band energy levels, the necessary logic operations completed and the interlock control signal generated. As shown in FIG. 4, the two curves correspond to the input optical detector signal 410, and, the resultant interlock control pulse 420. From this measurement, one can see that the delay time in this demonstration is only ≈29 nsec.

Hence, the observed 29 nsec delay in this demonstration establishes the minimum time delay required in the main laser leg of the system to assure same-pulse real-time spectral analysis. This rapid system response time greatly relaxes the constraints on the main laser pulse delay network, since 29 nsec corresponds to approximately 10 meters of free-space propagation, or, equivalently, transmission through 6 meters of optical fiber. In the case of free-space propagation, a compact White Cell of length 30 cm can provide the necessary delay time. Finally, this very rapid response time enables that overall interlock system to service high-repetition-rate pulsed laser systems, since the response time of the diagnostic sets an upper limit to the pulse-to-pulse period. In the present case, the 29 nsec delay can enable reliable operation of pulsed laser systems with rep rates on the order of 5 to 10 MHz.

In another set of experiments, using an operational three-stage laser, the overall system has been successfully demonstrated and shown to differentiate amongst laser pulses that meet (or exceed) a preset minimum spectral bandwidth from those pulses that do not; and, to subsequently control an optical interlock that passes or rejects each and every pulse in a given pulse sequence. The laser system used for this demonstration is similar to that shown in FIG. 1B consisting of three stages: a low-energy stage, comprised of a seed laser, a 60 GHz phase modulator and an optical preamplifier; an intermediate stage, comprised of a laser amplifier; and, a final stage, comprised of a high-power optical amplifier. As discussed, the 60 GHz modulator is used to add bandwidth to the laser pulse, which is required to circumvent optical damage. The presence of the modulated laser pulse thereby establishes the desired, or "acceptable," bandwidth for the interlock system to allow passage of the laser pulse to subsequent stages of the laser system. The "unacceptable" bandwidth condition corresponds to a situation whereby the laser pulse is not modulated; in this case, the laser bandwidth is determined solely by the bandwidth of the pulsed seed laser. To determine if the interlock, indeed, inhibits a given pulse from propagating beyond the interlock location, energy meters were positioned at each amplifier stage to record the measured laser energy, and, hence, to establish the presence or absence of a given laser pulse at that position.

Figure 5A:
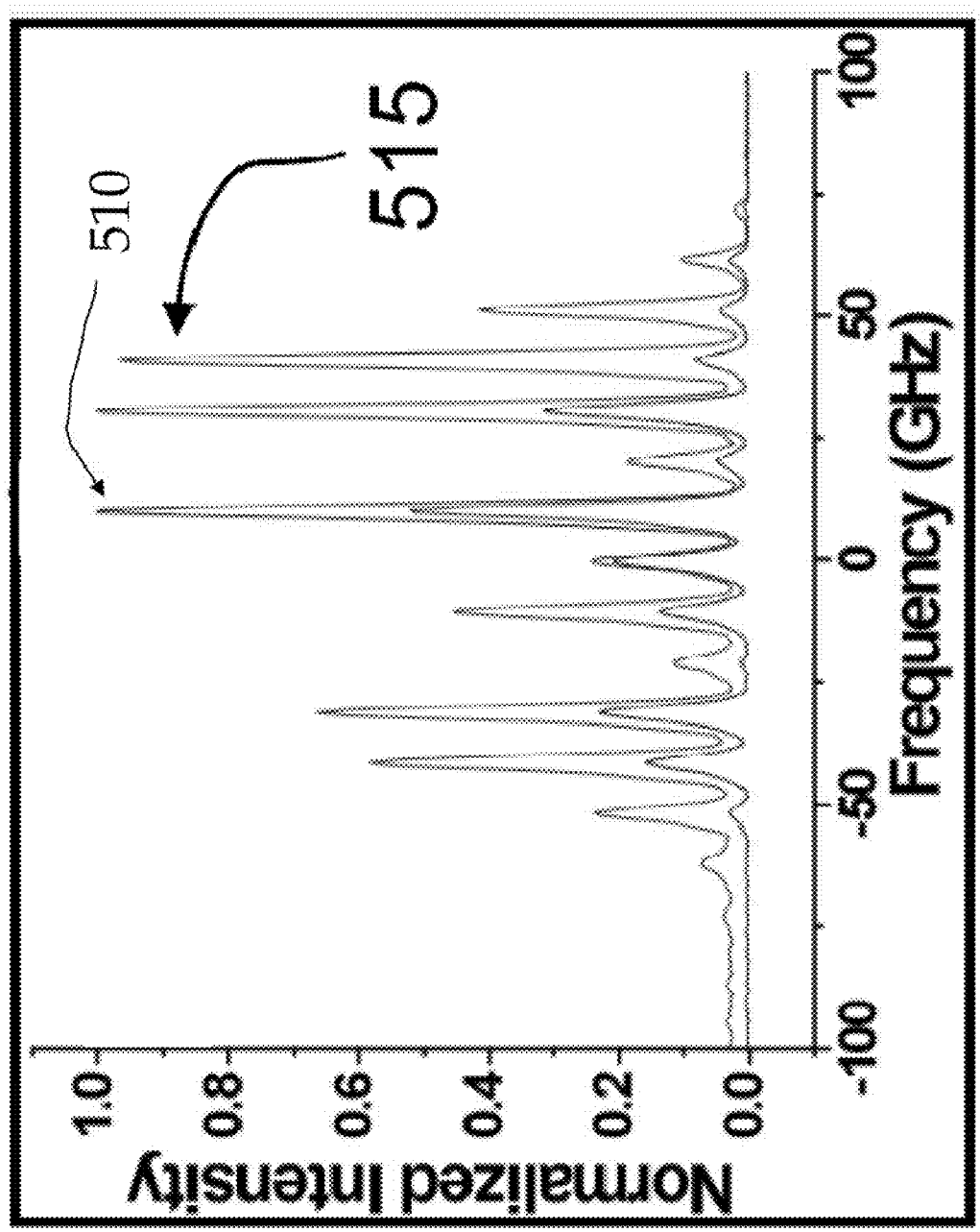
FIG. 5A shows the spectrum of the pulsed laser output without external modulation (defined as not meeting the minimum required bandwidth of the interlock system).
Figure 5B:
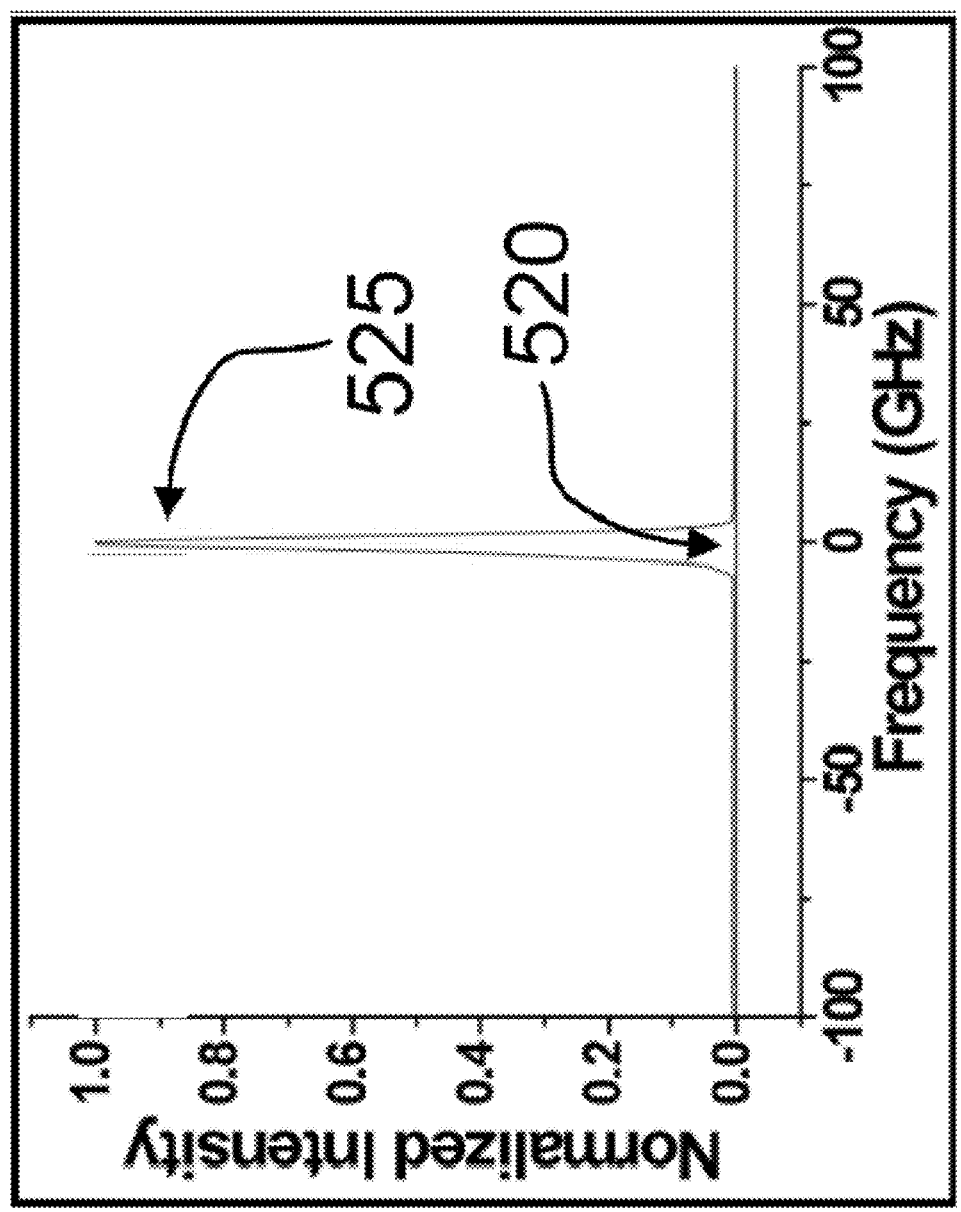
FIG. 5B displays the spectrum of the same pulsed laser in the case of a 60 GHz phase modulation signal imposed onto the beam (defined as satisfying the minimum bandwidth threshold of the system.
Figure 6A:
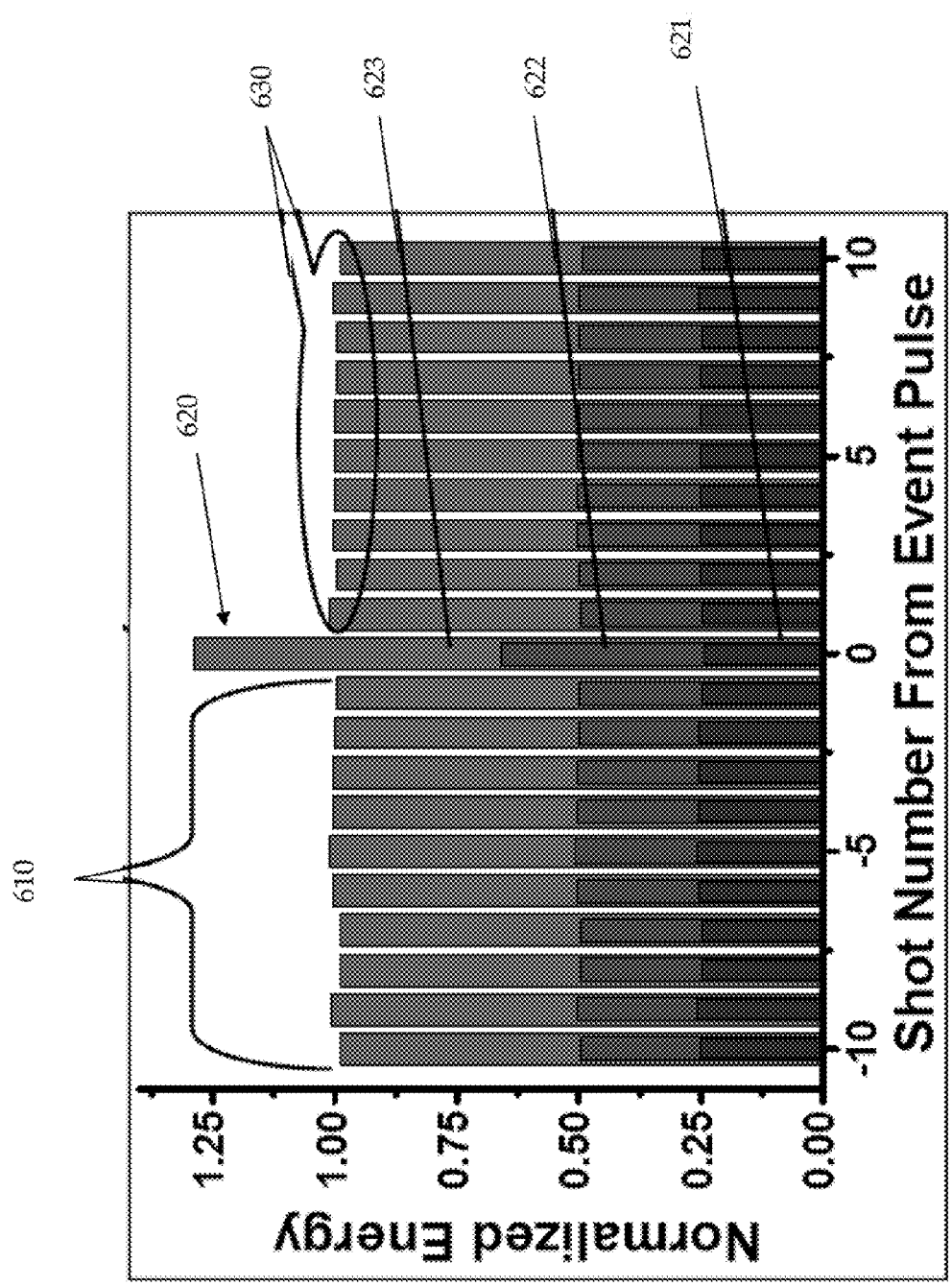
FIGS. 6A-6C show results of the interlock output for a given input sequence of laser pulses, with and without the imposed 60 GHz modulation, as shown in FIG. 5.
Figure 6B:
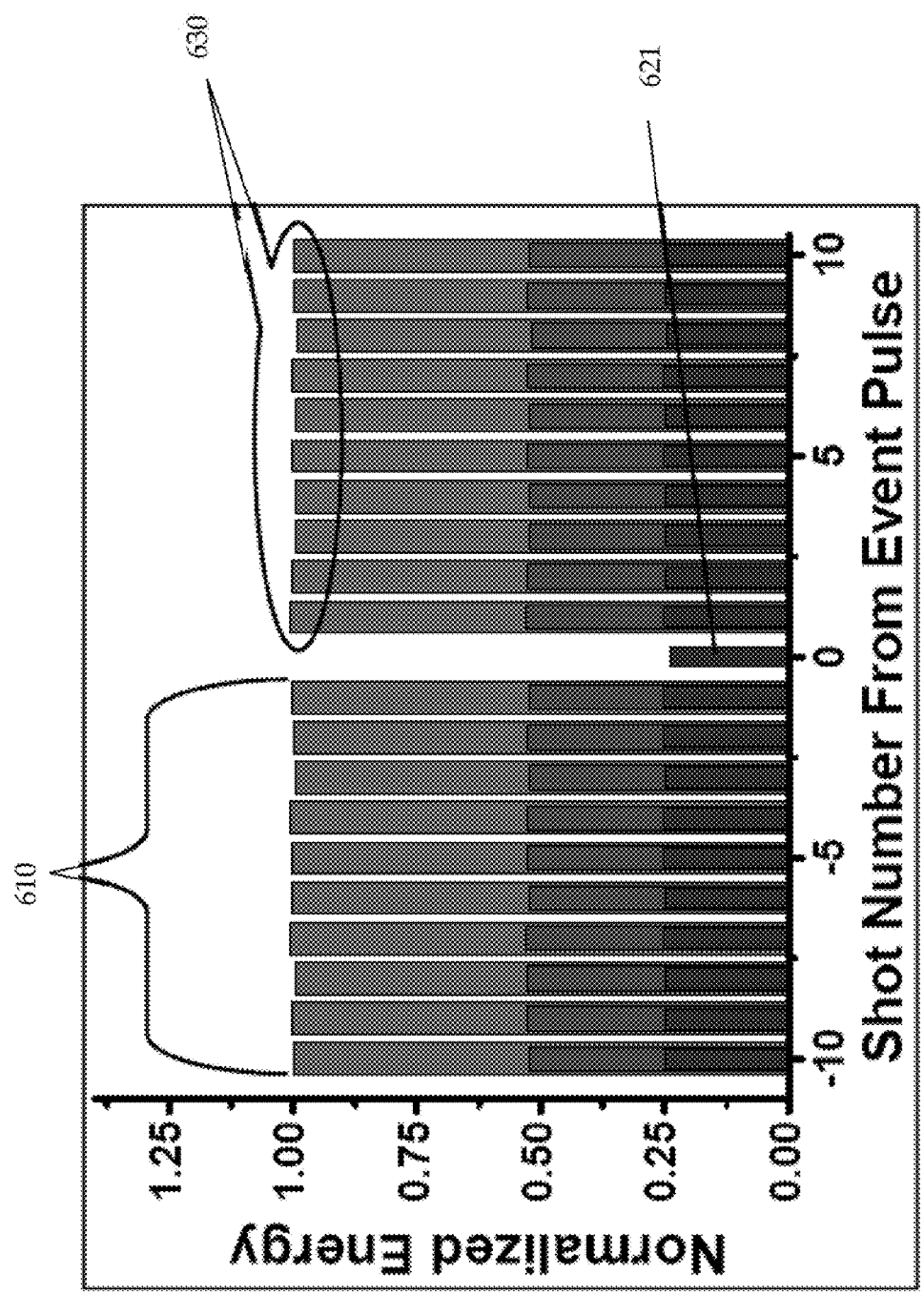
Figure 6C:
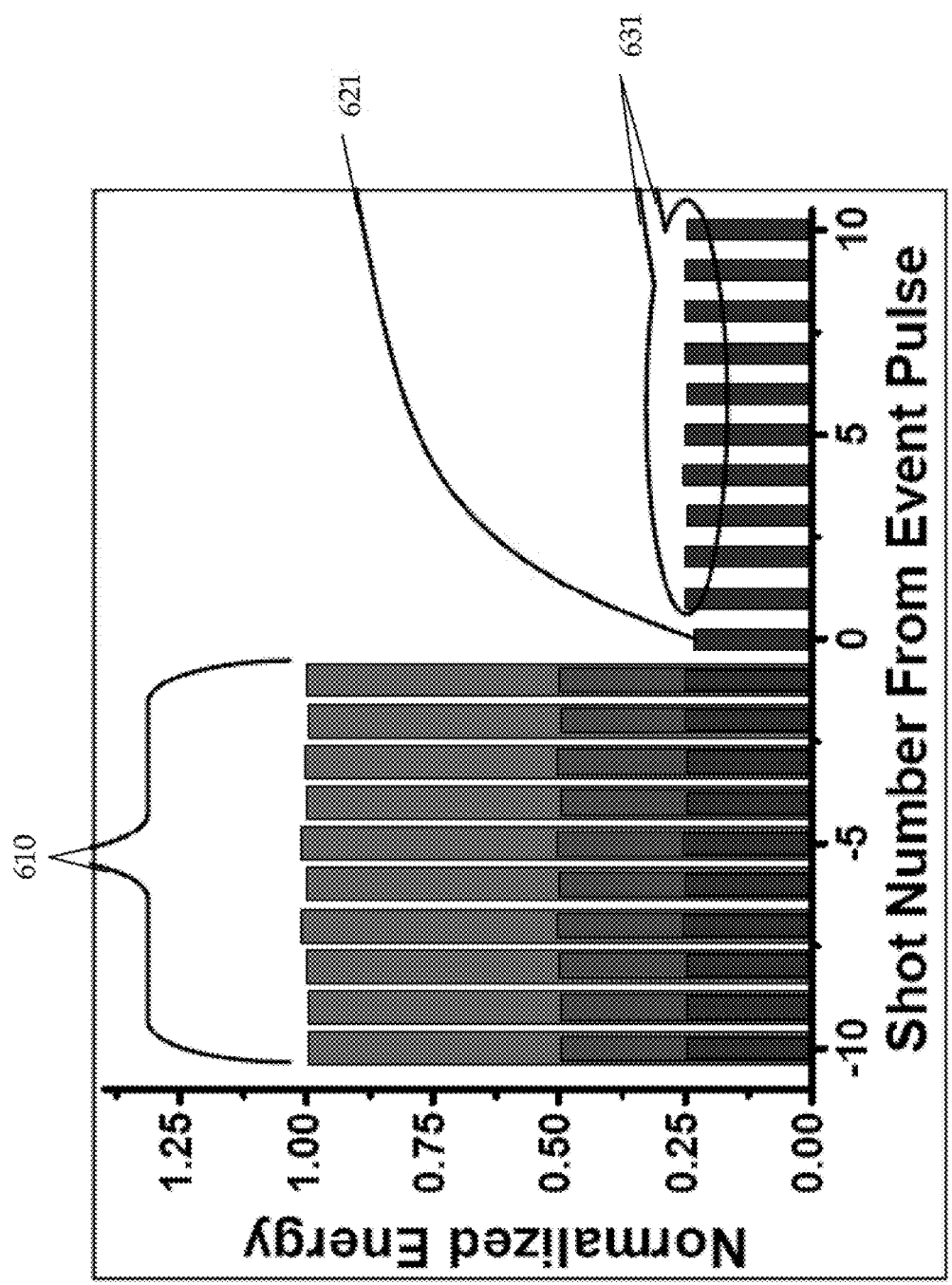

The results of this demonstration are shown in FIGS. 5A, 5B and 6. FIGS. 5A and 5B characterize the spectral bandwidth of two different input pulses generated to evaluate the system: a pulse that satisfies the preset bandwidth criterion (FIG. 5A) and a pulse that does not meet the minimum bandwidth requirement (FIG. 5B). FIGS. 6A-C show the response of the interlock system to a sequence of these pulses. In this demonstration, the system is operated using the two system modalities discussed above: the "latch mode" and the "auto-reset mode." Hence, for each modality, the interlock system is exposed to the same sequence of laser pulses, with the test sequence consisting of pulses that meet and do not meet the bandwidth criterion.

FIGS. 5A and 5B display the measured spectra generated by the first stage of the laser system. The spectra are chosen to define the "narrowband" and "wideband" pulses used for this demonstration. The pulses are generated using a pulsed laser, followed by a 60 GHz phase modulator. As discussed above, successful functioning of the interlock system to such a low modulation bandwidth is critical and extremely demanding, since the ability of the spectral analyzer to distinguish this relatively low bandwidth from that without modulation requires high-precision performance of its spectral dispersing capability; and, of course, the system reliance depends on zero false negatives (i.e., pulses that the interlock should eliminate, but, for whichever reason, allows to propagate further).

FIGS. 5A and 5B each display two spectra: the spectrum of the signal applied by the 60 GHz phase modulator, 515 and 525, respectively; and, the resultant laser pulse spectra, 510 and 520, respectively. In the "wide-bandwidth" case (FIGS. 5A), it is clearly seen that the laser spectrum faithfully reproduces the modulator spectrum, including its carrier and sideband features. In the narrow-bandwidth case (FIG. 5B), there is no signal applied to the modulator, hence the modulation spectrum is zero, as expected (525). In this case, the laser spectrum (520) is seen to be approximately the transform-limit of the raw output pulse, also, as expected.

FIGS. 6A, 6B and 6C display results of a demonstration of the three-stage MOPA laser system, with the spectral interlock module positioned between the first and second stages. For this demonstration the laser was triggered to generate a sequence of low and high bandwidth pulses, and, the performance of the spectral interlock system was evaluated, using several operational modalities. The results of this evaluation are shown as histograms of energy measurements recorded by the three energy meters (shown in FIG. 1B), 815, 825 and 835, with each placed at the output of each respective output stage of the laser system.

For this demonstration, the laser system is triggered to generate 21 pulses, with the relative energy of each laser pulse in the sequence recorded, for three different interlock operational modes: (1) the interlock diagnostic effectively out of the system; (2) the interlock diagnostic functioning in the "auto-reset mode"; and (3) the interlock diagnostic functioning in the "latch mode." In each histogram the same sequence of pulses are applied to the system. In each figure, every pulse was modulated at 60 GHz (acceptable bandwidth pulses), expect for event "0," in which case, the modulator was not activated. Specifically, there are 10 acceptable bandwidth pulses, followed by the un-modulated pulse, followed by another 10 acceptable pulses. The un-modulated pulse is referred to as "the event pulse," which would otherwise result in irreversible damage if not eliminated by the interlock system.

For each of the 21 laser shots, the laser energy was measured at three locations in the system, with each energy meter, 815, 825 and 835, positioned at the output point of each of respective stage, as shown in FIG. 1B: the seed laser/modulator/preamplifier stage; the intermediate amplifier stage; and the final amplifier output stage. In each case, a beam splitter ("B.S." in FIG. 1B) was used to sample a very small amount of energy for the relative energy measurements.

Turning to FIGS. 6A, 6B and 6C, a vertical bar is shown for each of the 21 laser pulses. Each vertical bar displays the normalized relative energy measurements from each of the three detectors for that given pulse. The lowest features on the vertical bars correspond to the recorded energy, 621, at the first-stage output, as recorded the energy meter 815. The central feature of the vertical bars correspond to the output of the intermediate amplifier stage, the energy level 622, recorded by energy meter 825; and, the upper portion, measured at the final-stage output, with a measured value 623, as recorded by energy meter 835.

For all these measurements, the bandwidth analysis module and the optical interlock hardware were both co-located at the output end of the first stage of the system, as shown in FIG. 1B. Therefore, as long as the laser successfully generated an output pulse, the first detector would indicate an energy level, regardless of the pulse bandwidth. However, assuming that the interlock system properly functioned, a rejected pulse would be prevented from continuing into the intermediate and final stages of the system, yet, still show an energy level for the first-stage detector.

FIG. 6A shows a histogram of the pulse events, all measured with the interlock system turned off. It is clearly seen that all the test pulses were present, each with output energy at each of the three respective stages of the system. The first 10 pulses 610 (events −10 to −1) were modulated at 60 GHz, the "0" event pulse 620 was not modulated, and the last 10 pulses 630 (events 1 to 10) were again modulated. The relatively higher energy measurements of the un-modulated "event pulse" is attributed to the physics of the system and is of no consequence so far as the operation of the interlock system is concerned (a slightly higher output energy would be expected for the narrow bandwidth pulse, since its bandwidth is presumably less than the homogeneous gain line-width of the amplifier stages, whereas with the 60 GHz modulation signal imposed onto the beam, the resultant pulse bandwidth presumably exceeds the homogeneous line-width of the amplifiers).

FIG. 6B shows a similar histogram as FIG. 6A, but now with the interlock system activated, and, further, operational in the "self-reset mode." As seen in this data, all pulses that met or exceeded the interlock system bandwidth criterion, 610 and 630, resulted in the expected optical energy values at all stages, consistent with that of the case where the interlock was not activated (recall FIG. 6A). However, it is clearly seen that the single pulse whose bandwidth did not satisfy the interlock criterion was eliminated, in accordance with the present invention. It is also clear from the figure that the seed laser indeed generated the pulse prior to the interlock, as seen by the energy output detected 621 at the output of the first stage of the laser system. Moreover, given that the interlock system was set to the "self-reset mode," it is seen that each pulse is considered, independent of the previous pulses. This is borne out by the fact that pulses subsequent to the failed event 0, whose bandwidth met the interlock criterion, were passed by the system 630.

Finally, FIG. 6C shows results of the case whereby the interlock system is set to the "latch mode." As discussed above, in this modality, the system will pass all pulses that meet the bandwidth conditions (610), until a pulse is evaluated that falls short of the desired condition. In this mode, if and when any pulse fails to meet the bandwidth criterion, that pulse (621), as well as all subsequent pulses (631), are prohibited from passing through the interlock; and, requires some form of intervention --- be it operator or algorithm or a combination thereof --- in order to reset the system to resume accepting bandwidth qualifying pulses once again. It is seen that the system functioned properly, since all initial pulses prior to the event pulse were passed by the interlock, whereas, the event pulse and all subsequent pulses (regardless of bandwidth) were rejected by the interlock. As a check that the seed laser successfully generated pulse throughout the sequence, it is seen that the narrow bandwidth pulse was, indeed, generated by this first stage, given its measured energy 621. And, furthermore, it is seen that all subsequent pulses also resulted in measured energy 631, thereby eliminating the possibility that the seed laser may have malfunctioned, which could have led to systematic errors.

Figure 7:
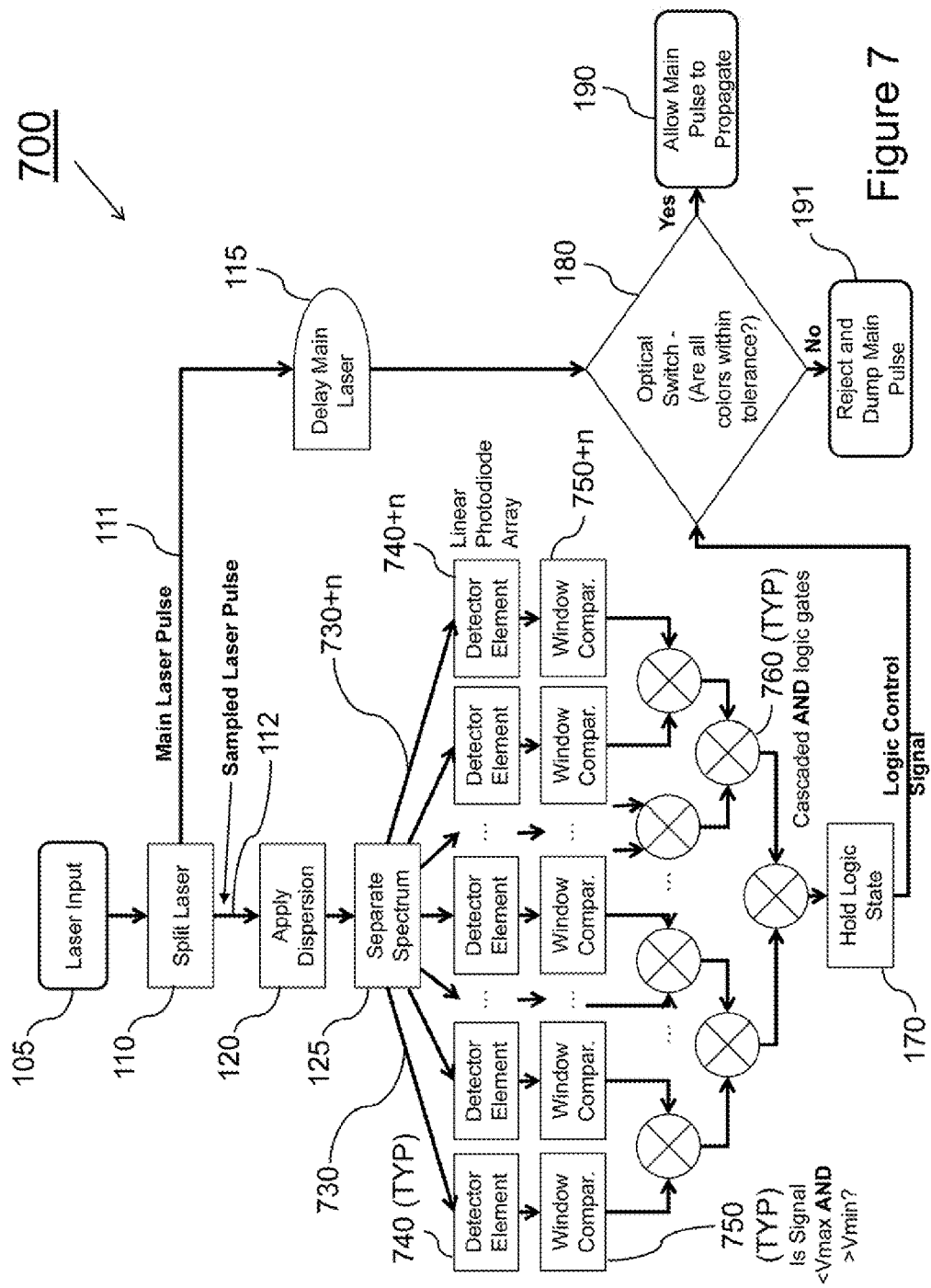
FIG. 7 shows a system flow chart of an exemplary embodiment of the present invention, configured to evaluate the shape of a pulse spectrum of a given laser pulse.

Turning now to FIG. 7, another embodiment of this invention is shown. This embodiment closely relates to that shown in FIG. 1A, which, recall, evaluates the extreme high and low wavelength regions of the optical spectrum of each pulse (and, optionally, the spectral midpoint band). In this present embodiment, the central wavelengths that emerge from the dispersive element are additionally partitioned into wavelength bands, with each such band referenced against a predefined optical level. This embodiment enables the interlock system to evaluate the spectral shape of each and every pulse, including the extreme high and low wavelength regions of the optical spectrum.

As shown in FIG. 7, the optical element 125 spatially partitions the pulse spectrum spectral components into spectral regions 730 to 730+n, where n+1 is the total number of such wavelength bands. Each of the n+1 bands is detected by a respective, dedicated fast photodiode 740 to 740+n, where n+1 is the total number of photodetectors, which is equal to the number of wavelength bands. Each wavelength band is adjustable in terms of its wavelength range and wavelength centroid, in an analogous manner as that shown in FIG. 2, the only difference being that the gap between the opposing prisms is set to zero, since all spectral components for each pair of wavelength hands is detected to ascertain the overall shape of the pulse spectrum.

The respective output levels from each detector are referenced against a respective comparator 750 to 750+n, where n+1 is equal to the total number of photodetectors. A logic level "1" is assigned to each comparator output if the optical signal is within the acceptable threshold range of levels; if not, a logic level "0" is assigned thereby. A tree configuration of logic-AND-gates evaluates the logic states of the comparators, with cascading tiers that ultimately results in a final tier comprised of a single gate. Specifically, the first tier of this configuration consists of an array of [(n+1)/2] logic-AND modules 760 that addresses respective pairs of comparator logic outputs (assumed to be an even number). This tier followed by a second tier of logic-AND modules that addresses respective pairs of gate output logic states from the preceding tier of such modules, and, so on, until a single logic gate address the final pair of logic states that immediately precede it.

The final logic-gate output then addresses a hold-logic module 170, and generates a logic control signal as shown in FIG. 7, with the remainder of the system configuration equivalent to that shown in FIG. 1A. Therefore, the optical interlock will only be activated if each respective spectral band detects an optical level that meets each respective optical level requirement for a given wavelength band, as preset for a specific and-user application. Given the programmability of digital logic elements, this interlock system can be remotely reconfigured to function as the initial embodiment as shown in FIG. 1A, so that only the extreme low and high-wavelength bands are interrogated. Moreover, as is the case of the initial embodiment, this embodiment can also be programmed to function in either an "auto-reset mode" or in a "latch mode."

The foregoing description of the invention has been presented for purposes of illustration and description and is not intended to be exhaustive or to limit the invention to the precise form disclosed. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

We claim:

1. A method, comprising:
providing an optical path including means for separating light into a spectrum, directing a first range of wavelengths to a first detector and directing a second range of wavelengths to a second detector, wherein said first range of wavelengths comprises relatively short wavelengths compared to said second range of wavelengths, wherein said second range of wavelengths comprises relatively long wavelengths compared to said first range of wavelengths;
splitting an input pulse of light into a first pulse and a second pulse;
directing said first pulse of light onto said optical path, wherein if said first pulse of light comprises wavelengths within said first range, said first detector will produce a first signal, wherein, if said first pulse of light comprises wavelengths of light within said second range, said second detector will produce a second signal; and
blocking said second pulse of light unless said first signal is produced by said first detector and said second signal is produced by said second detector.

2. The method of claim 1, wherein said means for separating light into a spectrum comprises two diffraction gratings.

3. The method of claim 1, wherein said first detector comprises a first high-speed photodiode and wherein said second detector comprises a second high-speed photodiode.

4. The method of claim 1, wherein the step of blocking is carried out with means for blocking a pulse of light.

5. The method of claim 4, wherein said means for blocking is configured to remain in a blocking mode only for a time period sufficient to block said second pulse.

6. The method of claim 4, wherein said means for blocking is configured to remain in a blocking mode until it is reset.

7. The method of claim 1, wherein said second pulse is delayed for a period of time sufficient for the step of blocking said second pulse to operate.

8. The method of claim 1, wherein if said first pulse of light comprises wavelengths within said first range and having a power level at least as great as a first preset threshold, said first detector will produce said first signal.

9. The method of claim 1, wherein if said first pulse of light comprises wavelengths of light within said second range and having a power level at least as great as a second preset threshold, said second detector will produce said second signal.

10. The method of claim 2, wherein said two diffraction gratings comprise two multi-layer dielectric coated diffraction gratings.

11. An apparatus, comprising:
an optical path including means for separating light into a spectrum, directing a first range of wavelengths to a first detector and directing a second range of wavelengths to a second detector, wherein said first range of wavelengths comprises relatively short wavelengths compared to said second range of wavelengths, wherein said second range of wavelengths comprises relatively long wavelengths compared to said first range of wavelengths;

means for splitting an input pulse of light into a first pulse and a second pulse;

means for directing said first pulse of light onto said optical path, wherein if said first pulse of light comprises wavelengths within said first range, said first detector will produce a first signal, wherein if said first pulse of light comprises wavelengths of light within said second range, said second detector will produce a second signal; and means for blocking said second pulse of light unless said first signal is produced by said first detector and said second signal is produced by said second detector.

12. The apparatus of claim 11, wherein said means for separating light into a spectrum comprises two diffraction gratings.

13. The apparatus of claim 11, wherein said first detector comprises a first high-speed photodiode and wherein said second detector comprises a second high-speed photodiode.

14. The apparatus of claim 11, wherein said means for blocking is configured to remain in a blocking mode only for a time period sufficient to block said second pulse.

15. The apparatus of claim 11, wherein said means for blocking is configured to remain in a blocking mode until it is reset.

16. The apparatus of claim 11, further comprising means for delaying said second pulse for a period of time sufficient for said means for blocking said second pulse to operate.

17. The apparatus of claim 11, wherein if said first pulse of light comprises wavelengths within said first range and having a power level at least as great as a first preset threshold, said first detector will produce said first signal.

18. The apparatus of claim 11, wherein if said first pulse of light comprises wavelengths of light within said second range and having a power level at least as great as a second preset threshold, said second detector will produce said second signal.

19. The apparatus of claim 12, wherein said two diffraction gratings comprise two multi-layer dielectric coated diffraction gratings.

* * * * *